United States Patent [19]

Boroschewski et al.

[11] 4,076,518

[45] Feb. 28, 1978

[54] SUBSTITUTED PHENYL THIOCARBAMATES WITH HERBICIDAL ACTION AND METHOD FOR THEIR PRODUCTION

[75] Inventors: Gerhard Boroschewski, Berlin; Friedrich Arndt, Aich, both of Germany

[73] Assignee: Schering Aktiengesellschaft, Berlin, Germany

[21] Appl. No.: 672,940

[22] Filed: Apr. 2, 1976

Related U.S. Application Data

[62] Division of Ser. No. 171,757, Aug. 13, 1971, abandoned.

[30] Foreign Application Priority Data

Aug. 20, 1970   Germany .............................. 2042110

[51] Int. Cl.$^2$ ...................... A01N 9/12; C07C 155/09
[52] U.S. Cl. .................................. 71/100; 260/455 A
[58] Field of Search ...................... 260/455 A, 471 C; 71/100

[56] References Cited

U.S. PATENT DOCUMENTS

| 3,404,975 | 10/1968 | Wilson et al. ................... 260/455 A |
| 3,532,738 | 10/1970 | Wilson et al. ................... 260/455 A |
| 3,701,646 | 10/1972 | Neighbors ....................... 260/455 A |
| 3,865,867 | 2/1975 | Olin et al. .............................. 71/100 |
| 3,879,441 | 4/1975 | Boroschewski et al. ........ 260/471 C |
| 3,901,936 | 8/1975 | Boroschewski et al. ........ 260/471 C |
| 3,904,669 | 9/1975 | Boroschewski et al. ........ 260/471 C |

FOREIGN PATENT DOCUMENTS

| 1,568,621 | 11/1965 | Germany ......................... 260/455 A |
| 1,567,151 | 4/1965 | Germany ......................... 260/455 A |

*Primary Examiner*—Delbert R. Phillips
*Attorney, Agent, or Firm*—Joseph F. Padlon

[57] ABSTRACT

Substituted phenyl thiocarbamates either per se or herbicides contain them and methods for their production are provided herein. Such compounds are available for destroying or inhibiting undesirable plant growth in cabbages.

10 Claims, No Drawings

SUBSTITUTED PHENYL THIOCARBAMATES WITH HERBICIDAL ACTION AND METHOD FOR THEIR PRODUCTION

This is a division of application Ser. No. 171,757, filed Aug. 13, 1971, now abandoned.

The invention relates to substituted phenyl thiocarbamates, herbicides containing these carbamides, as well as to methods for the production of these compounds.

The German display document DOS 1,567,151 already described m-bis-carbamates, among others methyl-N-(3-(N'-(3'-methylphenyl)-carbamoyloxy)-phenyl)-carbamate with herbicidal action. The herbicidal action of m-thiocarbanilates, for example, S-methyl-m -(methylcarbamoyl)oxy)-thiocarbanilate, is likewise known, for example, from DOS 1,568,621. It was found however, that these active substances have an extremely great selectivity to beet plants, but not to other cultivated plants, such as cabbage.

The object of the present invention is the development of herbicides which show, apart from their herbicidal action, a good tolerability to cultivated plants, like cabbage, and which are therefore particularly suitable for killing undesired plant growth in cabbage cultures. It was found that compounds of the general formula

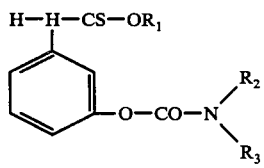

where R1 denotes a low alkyl, R2 hydrogen or a low alkyl, R3 an, if necessary substituted aliphatic, cyclo-aliphatic or aromatic hydrocarbon radical, and where R2 and R3 represent together with the N-atom a ring containing, if necessary, additional heteroatoms, display an excellent herbicidal action against weeds, while leaving at the same time cultivated plants, like various species of cabbage unharmed.

The subject matter of the invention concerns therefore new substituted phenyl thiocarbamates of the above indicated formula I, carbamates containing these herbicides, and methods for the production of these compounds.

By aliphatic hydrocarbon radicals characterized by the above formula it is understood, for example, straight chained and branched alkyl radicals, such as methyl-, ethyl-, propyl-, isopropyl-, butyl-, isobutyl-, tert. butyl-, pentyl-, hexyl-, neopentyl-, 1-methylbutyl-, sec. butyl-, 1,3-dimethylbutyl- and the 1,2-dimethyl-propyl radical, etc., and also unsaturated aliphatic hydrocarbon radicals, like alkenyl- and alkinyl radicals, for example, the allyl and butin-(1)-yl-(3) radical, etc.

These radicals may also be mono- or poly-substituted by halogen, like fluorine, chlorine or bromine; such as the 2chlorallyl-, 2-chlorethyl 2-bromethyl- and the 1-chloromethylbutyl radical.

As cycloaliphatic hydrocarbon radicals monocyclic and bicyclic radicals may be used, such as the cyclopropyl-, cyclopentyl-, cyclohexyl-, and methyl cyclohexyl- or the norbornyl radical, etc.

Aromatic hydrocarbon radicals such as phenyl- and the napthyl radical can be used. There also can be used the mono- or polysubstituted ones, preferably by alkyl, for example, methyl or halogen, such as chlorine, and/or alkoxy, such as methoxy.

Of the above mentioned compounds, those are particularly outstanding where R1 denotes methyl or ethyl, R2 hydrogen, methyl or ethyl, R3 alkyl with 1 to 8 carbon atoms, allyl, cyclohexyl, napthyl or phenyl mono- or polysubstituted, if necessary, by methyl and/or chlorine and/or methoxy, and where R2 and R3 together with the N-atom represent the pyrrolidino-, morpholinoor piperidino group.

It will be noted that the herbicidal properties of the compounds according to the invention are remarkable. Thus the action of a great many of their representatives extends both to the application in the pre- and in the after-emergence method, and thus they permit their application independently of the time of vegetation.

Of the numerous weeds which can be treated with the active substances of the invention, are for example, stellaria media, senecio vulgaris, matricaria chamomilla, lamium amplexicaule, galinsoga parviflora, chenopodium album, amarantus retroflexus, setaria italica, etc.

Most of the above mentioned active substances proved beyond that surprisingly to be selective to cultivated plants, for example, to various species of cabbage, so that they can be used there for the control of undesired plants without harming these cultures.

Weed control is also possible in the after-emergence method in the growing of products such as cauliflower, red cabbage, white cabbage and Brussels sprouts, where the cultivated plants are not affected even if they were to come in direct contact with the active substances or with the herbicides containing these substances.

The above indicated active substances can also be used for weed control in cultivated grasses, like seed or plant rice, corn or other types of grain.

The amounts necessary for an effective control in food plant cultures vary between 0.5 and 5 kg active substance/ha.

If the active substances are used in large quantities of more than 10 kg/active substance/ha, a total control of the undesired plant growth can be achieved.

As mentioned earlier, the above indicated active substances are characterized surprisingly by selectivity to various species of cabbage, compared to other known active substances.

The active substances can be used either alone or in mixture with other active substances. If necessary, other plant protectives or pest control agents can be added, for example, fungicides, nematocides, or other agents, depending on the desired result. The addition of fertilizers is also possible.

Other herbicides can also be added, where an extension of the action-spectrum or an increase of the herbicidal action can be achieved. The selectivity is naturally not always maintained. For example, suitable as herbicidal mixing partners are active substances from the group of the carbamidic and carbamidic carbamidie esters, of the substituted anilines and anilides, triazines, amino-triazolz, diazines, like uracils, aliphatic carboxylic acids, ureas, 2,3,6-trichlorobenzyloxy-propanol and acid, hydrazides, amides, nitriles, esters of these carboxylic acids, ureas, 2,3,6trichlorobenzyloxy-propanol and thiocyanogen-containing agents, etc.

The active substances are preferably used in the form of powders, pellets, solutions, emulsions or suspensions, with liquid and/or solid vehicles, or dilutants and if necessary wetting, adhesive, emulsifying and/or despersing agents.

By other additives are understood, for example, non-phytotoxic additives, which can yield a synergistic effect in herbicides, such as wetting agents, emulsifiers, solvents and oily additives.

As solid vehicles, there can be used, lime, kaolin, talcum, natural or synthetic silica, attaclay and other clays.

As surface active substances, salts of ligninsulfonic acid, salts of alkylated benzene-sulfonic acids, sulfonated acid amides and salts thereof, polyglycols, polyethoxylated amines, alcohols and phenols, may be used.

The portion of the active substances in the herbicide can vary within wide limits, such as where the herbicides can contain about 20% –80% by weight active substances, about 80 to 20% by weight liquid or solid vehicles and, if necessary, up to 20% by weight of surface active substances.

The hitherto unknown compounds of the formula

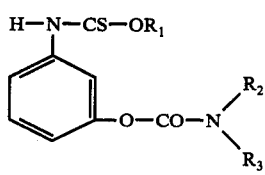

can be produced, for example, by reacting compounds of the general formula

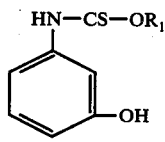

or their alkali salts, for example, the sodium salts, as follows: (a) with carbamoyl chlorides of the general formula

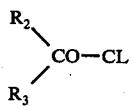

if necessary, in the presence of an acid acceptor, like a tert. organic base, like triethylamine, dimethyl aniline or pyridine; or
 (b) with phosgene, if necessary, in the presence of the acid acceptors mentioned under (a), to the corresponding chloroformic esters and reacting the latter with an amine of the general formula

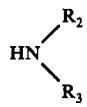

or
 (c) provided $R_2$ denotes hydrogen - with isocyanates of the general formula

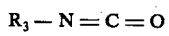

in the presence of a catalyst, like triethylamine, 1,4-diazabicyclo/2,2,2/-octane or dibutyl tin dilaureate.

According to another method, the compounds of the general formula (I) can be produced, for example, by reacting compounds of the general formula

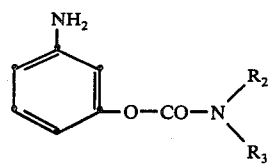

with chlorothioformic-O-alkyl esters of the general formula

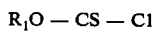

preferably in the presence of an organic or inorganic base, for example, triethylamine, N,N-dimethylaniline, magnesium oxide, sodium carbonate or sodium hydroxide.

The radicals $R_1$, $R_2$ and $R_3$ have the meaning indicated above in formula (I).

These reactions are brought about by using a solvent, such as tetrahydrofurane.

The starting products for carrying out the above described methods are known in themselves or can be produced according to known methods.

3-hydroxythiocarbanilic-O-alkyl esters can be obtained, for example, by reacting 3-hydroxyphenyl mustard oil with the corresponding alcohol in the presence of sodium alcoholate or by reacting 3-aminophenol with chlorthioformic-O-alkyl esters, if necessary, in the presence of an inorganic or organic base, such as triethylamine, N,N-dimethyl aniline, magnesium oxide, sodium carbonate or sodium hydroxide, 3-amino-phenyl carbamates; or on the other hand, by reducing the corresponding nitro compounds with hydrogen, using nickel catalysts.

The followig examples will illustrate the production of the starting compounds:

(1) 3-hydroxythiocarbanilic-O-methyl esters

To a solution of 1 mole sodium methylate in 0.5 l methanol are added in drops under stirring at 30 deg C, a solution of 75.6 g (0.5 mole) 3-hydroxyphenyl mustard oil in 100 ml methanol. After 1 day at room temperature, the mixture is poured on icehydrochloric acid, and the separated oil is taken up in ether. After drying with magnesium sulfate and evaporation of the ether, the evaporation residue is mixed with benzine. F. = 68° – 69° C Yield: 82.7 g = 90% of the theory (2) 3-hydroxy-thiocarbanilic-O-ethyl esters To a solution of 70.8 g (.065 mole) m-aminophenol in ab. 1 liter acetonitrile are added in drops under stirring at room temperature 35.2 g (0.325 mole) chlorthioformic-o-ethyl ester. After two days at room temperature the mixture is evaporated in the vacuum, the residue is dissolved in acetic ester, adding diluted hydrochloric acid. The organic phase is dried with magnesium sulfate, evaporated in the vacuum and recrystallized from benzene. F. = 106° – 107° C Yield 11.3 g = 17% of the theory.

The production of the compounds according to the invention results from the following examples.

(3)

O-methyl-N-(3-morpholinocarbonyloxyphenyl-thiocarbamate

From 12.8 g (0.07 mole) 3-hydroxythiocarbanilic-O-methyl ester, the sodium salt is produced with 0.07 mole sodium methylate in methanol. After evaporation of the methanol in the vacuum and drying of the sodium salt, the latter is mixed with 50 ml methyl-isobutyl ketone and solution of 10.4 g (0.07 mole) morpholic-N-carboxylic chloride in 40 ml methyl isobutyl ketone is added in drops under stirring within 10 minutes. After stirring for another hour at room temperature, washing with diluted hydrochloric acid and water and drying with magnesium sulfate, the product is evaporated. The residue crystallizes from ether/pentane. F. = 82°– 84° deg C Yield: 13.0 g = 63% of the theory.

(4) O-methyl-N-(3-(N', N'-diethylcarbamoyloxy-)-phenyl)-thiocarbamate

A solution of 18.3 g (0.1 mole) 3-hydroxythiocarbanilic-o-methyl ester and 14.9 g (0.11 mole) diethylcarbamoyl chloride in 90 ml dry pyridine are heated for 1 hour on the steam bath. Then the product is evaporated in the vacuum, the residue is dissolved in acetic ester/water, and the organic phase is washed at 0 deg C with diluted soda lye, water, diluted hydrochloric acid, water and sodium bicarbonate solution. After drying with magnesium sulfate, the product is evaporated in the vacuum. $nD^{20}$: 1.5963 Yield: 21.3 g = 76% of the theory

(5) O-methyl-N-(3-(N'-(3'-chlorphenyl)-carbamoyloxy)-phenyl)-thiocarbamate

A solution of 14.7 g (0.08 mole) 3-hydroxythiocarbanilic-O-methyl ester in 100 ml tetrahydrofurane is mixed with 13.1 g 3-chlorphenyl isocyanate and 0.5 ml triethyl amine. After 1 day benzine is added, after which the carbamate crystallizes.

F. = 116° – 118° C Yield 21.9 g = 82% of the theory

The following table contains additional compounds according to the invention.

| Compound No. | Name of Compound | Physical constant |
| --- | --- | --- |
| 1 | O-ethyl-N-(3-(N'-phenyl-carbamoyloxy)-phenyl)-thiocarbamate | F.=127.5–128.5° C |
| 2 | O-ethyl-N-(3-(N'-(3'-methylphenyl)-carbamoyloxy)-phenyl)-thiocarbamate | F.=93–94° C |
| 3 | O-ethyl-N-(3-(N'-(4'-methylphenyl)-carbamoyloxy)-phenyl)-thiocarbamate | F.=120–122° C |
| 4 | O-methyl-N-(3-(N'-phenyl-carbamoyloxy)-phenyl)-thiocarbamate | Harz |
| 5 | O-methyl-N-(3-(N'-(2'-methyl-phenyl)-carbamoyloxy)-phenyl)-thiocarbamate | Harz |
| 6 | O-methyl-N-(3-(N'-(4'-methylphenyl)-carbamoyloxy)-phenyl)-thiocarbamate | Harz |
| 7 | O-methyl-N-(3-(N'-(3'-methylphenyl)-carbamoyloxy)-phenyl)-thiocarbamate | Harz |
| 8 | O-methyl-N-(3-(N'-methyl-carbamoyloxy)-phenyl)-thiocarbamate | F.=115–116° C |
| 9 | O-methyl-N-(3-(N'-ethyl-carbamoyloxy)-phenyl)-thiocarbamate | F.=107–108° C |
| 10 | O-methyl-N-(3-(N'-tert.-butyl-carbamoyloxy)-phenyl)-thiocarbamate | F.=113–114° C |
| 11 | O-methyl-N-(3-(N'-cyclohexyl-carbamoyloxy)-phenyl)-thiocarbamate | F.=110–112° C |
| 12 | O-methyl-N-(3-(N'-(4'-chlorphenyl)-carbamoyloxy)-phenyl)-thiocarbamate | F.=157° C |
| 13 | O-methyl-N-(3-(N'-n-hexyl-carbamoyloxy)-phenyl)-thiocarbamate | Harz |
| 14 | O-methyl-N-(3-(N'-n-octyl-carbamoyloxy)-phenyl)-thiocarbamate | Harz |
| 15 | O-methyl-N-(3-(N'-(2',5'-dichlorphenyl)-carbamoyloxy)-phenyl)-thiocarbamate | F.=145–147° C |
| 16 | O-Methyl-N-(3-(N'-(3',4'-dichlorphenyl)-carbamoyloxy)-phenyl)-thiocarbamate | F.=158–160° C |
| 17 | O-methyl-N-(3-(N'-isopropylcarbamoyloxy)-phenyl)-thiocarbamate | F.=123–126° C |
| 18 | O-methyl-N-(3-(N'-n-butylcarbamoyloxy)-phenyl)-thiocarbamate | F.=62–64° C |
| 19 | O-methyl-N-(3-(N'-allylcarbamoyloxy)-phenyl)-thiocarbamate | F.=71–72° C |
| 20 | O-methyl-N-(3-(N'-(3'-methoxyphenyl)-carbamoyloxy)-phenyl)-thiocarbamate | F.=93–95° C |
| 21 | O-methyl-N-(3-(N'-neopentylcarbamoyloxy)-phenyl)-thiocarbamate | F.=121–122° C |
| 22 | O-methyl-N-(3-(N'-(3',5'-dimethylphenyl)-carbamoyloxy)-phenyl)-thiocarbamate | F.=108–109.5° C |
| 23 | O-methyl-N-(3-(N'-(3',4'-dimethylphenyl)-carbamoyloxy)-phenyl)-thiocarbamate | F.=110–111° C |
| 24 | O-methyl-N-(3-(N'-(2',5'-dimethylphenyl)-carbamoyloxy)-phenyl)-thiocarbamate | F.=155–156° C |
| 25 | O-methyl-N-(3-(N'-2',3'-dimethylphenyl)-carbamoyloxy)-phenyl)-thiocarbamate | F.=157–158° C |
| 26 | O-methyl-N-(3-(N'-isobutylcarbamoyloxy)-phenyl)-thiocarbamate | F.=103° C |
| 27 | O-methyl-N-(3-(N'-pentyl(2)-carbamoyloxy)-phenyl)-thiocarbamate | F.=83–84.5° C |
| 28 | O-methyl-N-(3-(N'-(a-napthyl)-carbamoyloxy)-phenyl)-thiocarbamate | F.=159° C |
| 29 | O-methyl-N-(3-pyrrolidinocarbonyloxy)-phenyl)-thiocarbamate | F.=97–99° C |
| 30 | O-methyl-N-(3-piperidinocarbonyloxy-phenyl)-thiocarbamate | F.=105–106° C |
| 31 | O-methyl-N-(3-(N'-methyl-N'-phenyl-carbamoyloxy)-phenyl)-thiocarbamate | Harz |
| 32 | O-methyl-N-(3-(N'-(4'-fluorphenyl)-carbamoyloxy)-phenyl)-thiocarbamate | F.=125–126° C |
| 33 | O-methyl-N-(3-(N'-(3'-fluorphenyl)-carbamoyloxy)-phenyl)-thiocarbamate | F.=116–118° C |
| 34 | O-methyl-N-(3-(N'-(4'-jodphenyl)-carbamoyloxy)-phenyl)-thiocarbamate | F.=135–137° C |
| 35 | O-methyl-N-(3-(N'-(3'-jodphenyl)-carbamoyloxy)-phenyl)-thiocarbamate | $nD_{20}$=1.6500 |
| 36 | O-methyl-N-(3-(N'-(3'-trifluormethyl-phenyl)-carbamoyloxy)-phenyl)-thiocarbamate | F.=127° C |
| 37 | O-methyl-N-(3-(N'-sek.-butylcarbamoyloxy)-phenyl)-thiocarbamate | F.=99–100° C |
| 38 | O-methyl-N-(3-(N'-b-chlorethylcarbamoyloxy)-phenyl)-thiocarbamate | F.=87–89° C |
| 39 | O-methyl-N-(3-(N'-b-bromethylcarbamoyloxy)-phenyl)-thiocarbamate | Harz |

These are mostly crystalline substances which are soluble in acetic ester, acetone, tetrahydrofurane, dimethyl formamide and methylene chloride, etc.

The following examples show the herbicidal action of the compounds according to the invention, while the plants were not damaged by the reference agent.

The evaluation was made 3 weeks after the treatment, 0 indicating totally destroyed and 10 not damaged.

| No. | Agents According to the invention | Tomatoes | Sugar beets |
|---|---|---|---|
| 1 | O-methyl-N-(3-(N'-(4'-fluorphenyl)-carbamayloxy)-phenyl)-thiocarbamate | 0 | 0 |
| 2 | O-methyl-N-(3-piperidinocarbonyloxy-phenyl)-thiocarbamate | 0 | 2 |
| 3 | O-methyl-N-(3-morpholinocarbonyloxy-phenyl)-thiocarbamate | 2 | 2 |
| 4 | O-methyl-N-(3-pyrrolidinocarbonyloxy-phenyl)-thiocarbamate | 1 | 0 |
| 5 | O-ethyl-N-(3-(N'-(3'-methylphenyl)-carbamoyloxy)-phenyl)-thiocarbamate | 0 | — |
| 6 | O-ethyl-N-(3-(N'-(4'-methylphenyl)-carbamoyloxy)-phenyl)-thiocarbamate | 0 | — |
| 7 | O-methyl-N-(3-(N'-phenylcarbamoyloxy)-phenyl)-thiocarbamate | 0 | 1 |
| 8 | O-methyl-N-(3-(N'-(2'-methylphenyl)-carbamoyloxy)-phenyl)-thiocarbamate | 0 | 3 |
| 9 | O-methyl-N-(3-(N'-(4'-methylphenyl)-carbamoyloxy)-phenyl)-thiocarbamate | 0 | — |
| 10 | O-methyl-N-(3-(N'-(3'-methylphenyl)-carbamoyloxy)-phenyl)-thiocarbamate | 0 | 0 |
| 11 | O-methyl-N-(3-(N'-methylcarbamoyloxy)-phenyl)-thiocarbamate | 0 | 0 |
| 12 | O-methyl-N-(3-(N'-ethylcarbamoyloxy)-phenyl)-thiocarbamate | 3 | 0 |
| 13 | O-methyl-N-(3-(N'-tert. butylcarbamoyloxy)-phenyl)-thiocarbamate | 0 | 0 |
| 14 | O-methyl-N-(3-(N'-cyclohexylcarbamoyloxy)-phenyl)-thiocarbamate | 0 | 0 |
| 15 | O-methyl-N-(3-(N'-(3-chlorphenyl)-carbamoyloxy)-phenyl)-thiocarbamate | 2 | — |
| 16 | O-methyl-N-(3-(HN'-(4'-chlorphenyl)-carbamoyloxy)-phenyl)-thiocarbamate | 3 | 5 |
| 17 | O-methyl-N-(3-(N'-n-hexylcarbamoyloxy)-phenyl)-thiocarbamate | 0 | 0 |
| 18 | O-methyl-N-(3-(N'-n-octylcarbamoyloxy)-phenyl)-thiocarbamate | 0 | 0 |
| 19 | O-methyl-N-(3-(N'-isopropylcarbamoyloxy)-phenyl)-thiocarbamate | 0 | 0 |
| 20 | O-methyl-N-(3-(N'-n-butylcarbamoyloxy) phenyl)-thiocarbamate | 4 | 0 |
| 21 | O-methyl-N-(3-(N'-allylcarbamoyloxy)-phenyl)-thiocarbamate | 5 | 0 |
| 22 | O-methyl-N-(3-(N'-(3'-methoxyphenyl)-carbamoyloxy)-phenyl)-thiocarbamate | 0 | 0 |
| 23 | O-methyl-N-(3-(N',N'-diethylcarbamoyloxy)-phenyl)-thiocarbamate | 5 | 1 |
| 24 | O-methyl-N-(3-(N'-neopentylcarbamoyloxy)-phenyl)-thiocarbamate | 0 | 0 |
| 25 | O-methyl-N-(3-(N'-isobutylcarbamoyloxy)-phenyl)-thiocarbamate | 4 | 0 |
| 26 | O-methyl-N-(3-(N'-pentyl-(2)-carbamoyloxy)-phenyl)-thiocarbamate | 0 | 0 |
| Reference agent isopropyl-N-(3-(chlorphenyl)-carbamate | | 9 | 10 |
| untreated | | 10 | 10 |

10 = not damaged, 0 = totally destroyed the compounds according to the invention, compared to the known herbicides.

EXAMPLE 1

The tests plants listed below were treated in the hot house in the after-emergence method with the herbicides according to the invention in a dosage of 5 kg active substance/ha. The herbicides were sprayed evenly as aqueous suspensions with 600 liter/ha. The reference agent was used as an aqueous emulsion, likewise with 600 liter/ha.

The findings show that a destruction of substantial damage of the test plants could only be achieved with

EXAMPLE 2

Planted white cabbage and Brussels sprouts as well as various weeds were treated in the hot house in a dosage of 1 kg active substance/ha. The herbicides were to this end sprayed evenly on the plants as aqueous suspensions with 600 liter/ha. The results show that the compound according to the invention destroyed only the weeds, while the cultivated plants were not damaged. The known reference agent, on the other hand, destroyed not only the weeds but also caused heavy damage to the cabbage plants.

| | 1 | 2 | 3 | 4 | 5 | 6 | 7 |
|---|---|---|---|---|---|---|---|
| Agent according to the invention O-methyl-N-(3-N'-(3-methylphenyl)-carbamoyloxy)-phenyl)-thiocarbamate | 10 | 10 | 0 | 0 | 1 | 0 | 1 |
| Reference agent methyl-N-(3-(N'-(3-methylphenyl)- | | | | | | | |

| | 1 | 2 | 3 | 4 | 5 | 6 | 7 |
|---|---|---|---|---|---|---|---|
| carbamoyloxy)-phenyl)-carbamate | 5 | 2 | 0 | 0 | 1 | 0 | 1 |
| untreated | 10 | 10 | 10 | 10 | 10 | 10 | 10 |

1-white cabbage; 2-Brussels sprouts; 3-stellaria media; 4-senecio vulgaris; 5-marticaria chamomilla; 6-lamium amplexicaule; 7-ceutaurea cyanus

EXAMPLE 3

Planted cauliflower, red cabbabge and white cabbage were treated in the hot house with a dosage of 0.5 kg active substance/ha. The herbicides were sprayed to this end evenly on the plants as aqueous emulsions with 500 liter/ha. The results show that, unlike the reference compounds, the compound according to the invention displays a good tolerability to various species of cabbage.

| Agent according to the invention | Brussels sprouts | Red cabbage | white cabbage |
|---|---|---|---|
| O-methyl-N-(3-N'-(3'-methylphenyl)-carbamoyloxy)-phenyl)-thiocarbamate | 10 | 10 | 10 |
| Reference agent S-methyl-m-((methylcarbamoyl)-oxy)-thiocarbanilate | 1 | 3 | 3 |
| 2-methylthio-4-isopropylamino-6-methylamino-1,3,5-triazine | 0 | 2 | 3 |
| untreated | 10 | 10 | 10 |

We claim:

1. A method for the protection of cabbage plantations against infestation by weeds which comprises treatment of the plantation with a compound of the formula:

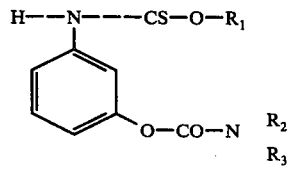

In which $R_1$ is methyl or ethyl, $R_2$ is hydrogen, methyl, or ethyl, $R_3$ is an alkyl radical having from 1 to 8 carbon atoms or a radical selected from the group consisting of allyl, cyclohexyl, napthyl, and phenyl radicals said compound being employed in an amount sufficient to control growth of weeds without causing significant damage to cabbage plants.

2. The method of claim 1 wherein the compound is O-ethyl-N-(3-(N'-phenylcabbamoyloxy)-phenyl)-thiocarbamate.

3. The method according to claim 1 wherein the compound is O-ethyl-N(3-(N'-(3'-methylphenyl)-carbamoyloxy)-phenyl)-thiocarbamate.

4. The method of claim 1 wherein the compound is O-ethyl-N-(3-(N'-(4'-methylphenyl)-carbamoyloxy)-phenyl)-thiocarbamate.

5. The method of claim 1 wherein the compound is O-methyl-N-(3-N'-phenyl-carbamoyloxy)-phenyl)-thiocarbamate.

6. The method of claim 1 wherein the compound is O-methyl-N-(3-(N'-2'-methylphenyl)carbamoyloxy)-phenyl)-thiocarbamate.

7. The method of claim 1 wherein the compound is O-methyl-N-(3-(N'-(4'-methylphenyl)-carbamoyloxy)-phenyl)-thiocarbamate.

8. The method of claim 1 wherein the compound is O-methyl N-(3-N'-methylcarbamoyl-oxy)-phenyl)-thiocarbamate.

9. The method of claim 1 wherein the compound is O-methyl-N-(3-N'-ethylcarbamoyloxy)-phenyl)-thiocarbamate.

10. The method of claim 1 wherein the compound is O-methyl-N-(3-(N'-tert.-butylcarbamoyloxy)-phenyl)-thiocarbamate.

* * * * *